United States Patent
Pomares Marco et al.

(10) Patent No.: US 12,172,979 B2
(45) Date of Patent: Dec. 24, 2024

(54) PROCESS FOR THE PREPARATION OF ARIPIPRAZOLE LAUROXIL

(71) Applicant: INTERQUIM, S.A., Sant Cugat del Vallès (ES)

(72) Inventors: Marta Pomares Marco, Sant Cugat del Vallès (ES); Francisco De Asís Marquillas Olondriz, Sant Cugat del Vallès (ES); Jorge Bessa Bellmunt, Bellaterra (ES); Antonio Abelino De León Martín, Bellaterra (ES)

(73) Assignee: INTERQUIM, S.A., Barcelona (ES)

( * ) Notice: Subject to any disclaimer, the term of this patent is extended or adjusted under 35 U.S.C. 154(b) by 653 days.

(21) Appl. No.: 17/501,152

(22) Filed: Oct. 14, 2021

(65) Prior Publication Data

US 2022/0064143 A1   Mar. 3, 2022

Related U.S. Application Data

(62) Division of application No. 16/633,757, filed as application No. PCT/EP2018/070511 on Jul. 27, 2018, now abandoned.

(30) Foreign Application Priority Data

Jul. 28, 2017  (EP) .................................. 17382509
Feb. 16, 2018  (EP) .................................. 18382091

(51) Int. Cl.
   C07D 401/12   (2006.01)
   G01N 30/72    (2006.01)

(52) U.S. Cl.
   CPC ....... *C07D 401/12* (2013.01); *G01N 30/7233* (2013.01)

(58) Field of Classification Search
   CPC .................................................. C07D 401/12
   See application file for complete search history.

(56) References Cited

FOREIGN PATENT DOCUMENTS

WO   WO 2008/132139 A2   11/2008
WO   WO 2010/151711 A1   12/2010
WO   WO 2018/104953 A1   6/2018

OTHER PUBLICATIONS

Bartlett "Exploiting Chemical Diversity for Drug Discovery" Edited by Paul A Bartlett and Michael Entzeroth, The Royal Society of Chemistry, 2006, pp. 113-118.*
"Find ETDs Home » Thesis Resources » Find ETDs" Online: "https://ndltd.org/thesis-resources/find-etds/" Accessed Jan. 31, 2023.*
Irwin "ZINC—A Free Database of Commercially Available Compounds for Virtual Screening" J. Chem. Inf. Model. 2005, 45, 177-182.*
Kim "PubChem in 2021: new data content and improved web interfaces" Nucleic Acids Research, 2021, vol. 49, Database issue Published online Nov. 5, 2020.*
STN Registry/Zregistry (CAS RegistrySM) Sep. 2016 2 pages.*
Advisory Action issued in U.S. Appl. No. 16/633,757, dated Jul. 9, 2021.
Final Office Action issued in U.S. Appl. No. 16/633,757, dated Mar. 26, 2021.
Foreign Priority Document filed Dec. 7, 2016 for WO 2018/104953 (Year: 2018).
International Search Report for PCT/EP2018/070511 mailed on Nov. 22, 2018.
Non-Final Office Action issued in U.S. Appl. No. 16/633,757, dated Sep. 17, 2020.
Written Opinion of the International Searching Authority (forms PCT/ISA/237 and PCT/ISA/220), dated Nov. 22, 2018, for corresponding International Application No. PCT/EP2018/070511.

* cited by examiner

*Primary Examiner* — Nizal S Chandrakumar
(74) *Attorney, Agent, or Firm* — Birch, Stewart, Kolasch & Birch, LLP

(57) ABSTRACT

It is provided a process for the preparation of aripiprazole lauroxil that comprises reacting 1-(hydroxymethyl) aripiprazole with lauric acid in the presence of a suitable solvent and a carboxyl activating agent in the presence of a suitable solvent and, optionally, in the presence of an appropriate base. 1-(Hydroxymethyl) aripiprazole can be prepared by reacting aripiprazol or an hydrate thereof with paraformaldehyde in the presence of a suitable organic solvent and a suitable base, wherein the reaction is carried out without the addition of water as a solvent to the reaction mixture. Additionally, (7-(4-(4-(2,3-dichlorophenyl)piperazin-1-yl) butoxy)-3,4-dihydro-2-oxoquinolin-1(2H)-yl)methyl formate is provided as a reference standard.

2 Claims, No Drawings

PROCESS FOR THE PREPARATION OF ARIPIPRAZOLE LAUROXIL

This application is a Divisional of co-pending application Ser. No. 16/633,757, filed on Jan. 24, 2020, which is the National Stage Application under 35 U.S.C. § 371 of International Application No. PCT/EP2018/070511, filed on Jul. 27, 2018, which claims the benefit of European Patent Application No. 17382509.2 filed on Jul. 28, 2017 and of European Patent Application No. 18382091.9 filed on Feb. 16, 2018, all of which are hereby expressly incorporated by reference into the present application.

TECHNICAL FIELD

The present invention relates to a process for the preparation of aripiprazole lauroxil, as well as to a side product from the synthesis of aripiprazole lauroxil and its use as a reference standard for analysis of aripiprazole lauroxil.

BACKGROUND ART

Aripiprazole is the generic name of compound 7-[4-[4-(2,3-dichlorophenyl)-1-piperazinyl]-butoxy]-3,4-dihydro-carbostyril, the chemical structure of which is the following:

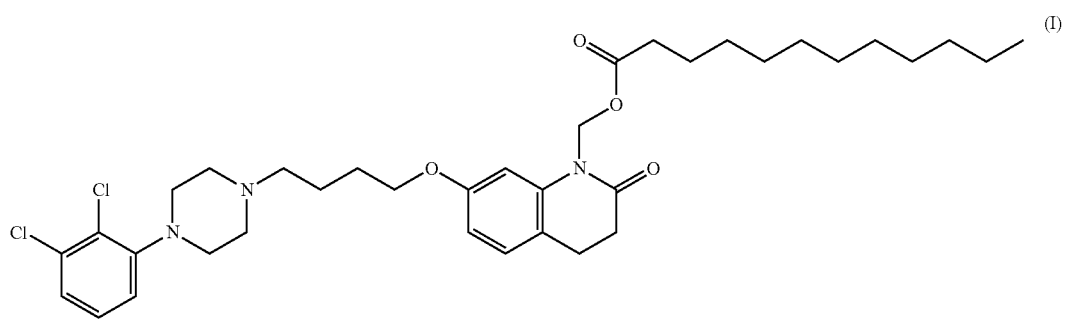 [SMILES: CCCCCCCCCCCC(=O)OCN1C(=O)CCc2ccc(OCCCCN3CCN(c4cccc(Cl)c4Cl)CC3)cc21]

Aripiprazole, which was first disclosed in document EP367141, is a third-generation antipsychotic agent useful in the treatment of schizophrenia, acute mania, bipolar disorder and other CNS disorders. Aripiprazole has been formulated for oral administration as a tablet and as a solution. However, concerns with patient compliance with oral antipsychotics have been reported, and other routes of administration, such as intramuscular or subcutaneous injection, have been developed.

Thus, formulations containing an aripiprazole prodrug that when administered to a patient can provide for improved therapeutic amounts of aripiprazole over an extended period of time, as well as methods of preparing said aripiprazole prodrug have been developed.

Particularly, documents WO2010151689 and WO2016032950, among others, disclose the preparation of aripiprazole lauroxil, this compound having the following chemical structure:

(I)

Nevertheless, overall yields reported are very low.

In view of the processes disclosed in the prior art, there is a need in the art for alternative processes for preparing aripiprazole lauroxil providing better yields and which are cost-effective and easy to scale-up to an industrial level.

SUMMARY OF INVENTION

Inventors have found a new process for the preparation of aripiprazole lauroxil that overcomes the drawbacks of the processes disclosed in the prior art.

Particularly, inventors have found that by reacting a compound of formula (II)

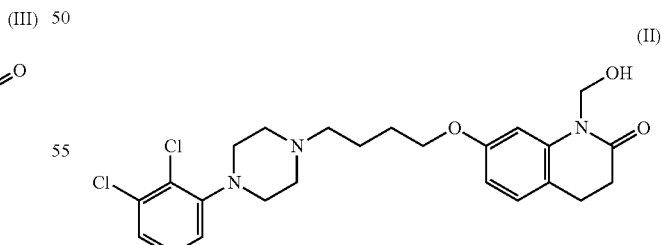

with lauric acid to obtain aripiprazole lauroxil notoriously good yields and purities are obtained.

Accordingly, an aspect of the present invention refers to a process for the preparation of a compound of formula (I)

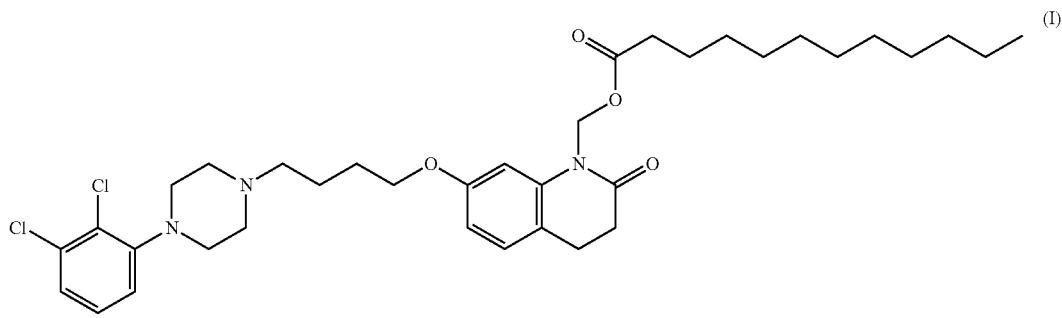 [SMILES: CCCCCCCCCCCC(=O)OCN1C(=O)CCc2ccc(OCCCCN3CCN(c4cccc(Cl)c4Cl)CC3)cc21]

which is aripiprazole lauroxil, which comprises reacting a compound of formula (II)

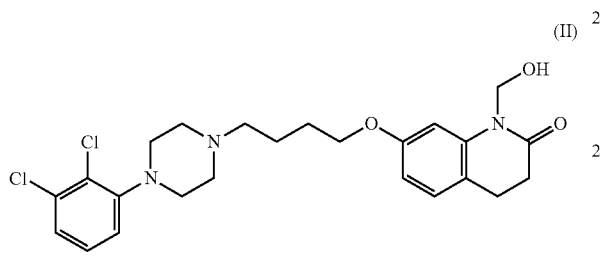

with lauric acid and a carboxyl activating agent in the presence of a suitable solvent and, optionally, in the presence of an appropriate base, to obtain aripiprazole lauroxil.

Additionally, the inventors have observed that when compound of formula (II) is obtained in the absence of water by reacting aripiprazole with paraformaldehyde (instead of formaldehyde) the starting product aripiprazole is found in the final product as an impurity in a relatively low percentage compared with the processes of the prior art. Particularly, as shown in Example 1 of WO2010151689, by carrying out the reaction with formaldehyde (37% aqueous solution) a 25% of aripiprazole is found in the final product, being the conversion into compound of formula (II) of only a 65%. Conversely, by carrying out the process in the absence of water, or in the presence of an amount of water equal to or lower than 1 wt %, as can be seen in Examples 1 to 3 of the invention, conversions higher than 77% are obtained. Thus, by the process of the invention the amount of aripiprazole is low enough to allow an easy purification of the final product such as by crystallization.

Accordingly, a process for the preparation of the compound of formula (II) comprising reacting aripiprazole of formula (III), or a hydrate thereof such as aripiprazol monohydrate, with paraformaldehyde in the presence of a suitable organic solvent and a suitable base, wherein the process is carried out either in the absence of water or in the presence of a content of water which comes from either the use of a non-anhydrous organic solvent, non-anhydrous reactants, or the use of a hydrated form of aripiprazole such as the monohydrate, without addition of further water, also forms part of the invention.

Another aspect of the present invention relates to a process for the preparation of a compound of formula (I), which is aripiprazole lauroxil,

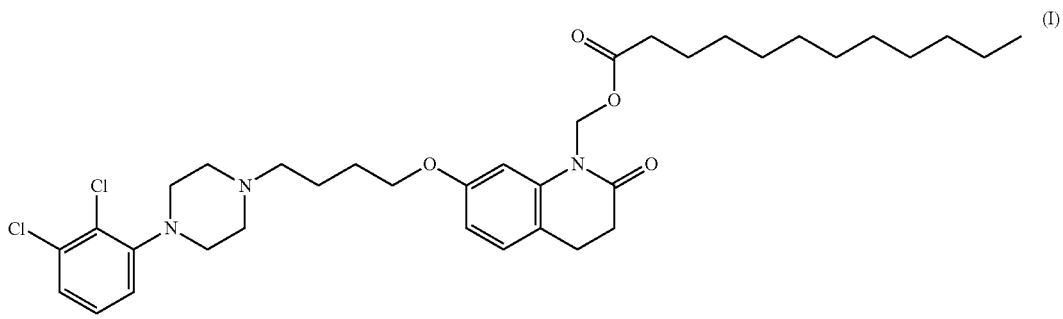 [SMILES: CCCCCCCCCCCC(=O)OCN1C(=O)CCc2ccc(OCCCCN3CCN(c4cccc(Cl)c4Cl)CC3)cc21]

which comprises the steps of:

a) preparation a compound of formula (II)

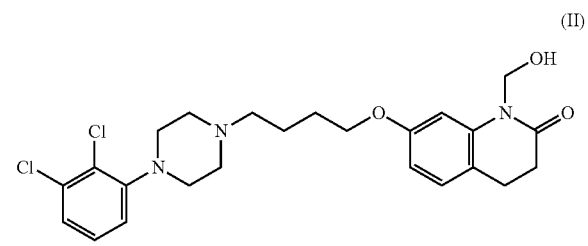 [SMILES: O=C1CCc2ccc(OCCCCN3CCN(c4cccc(Cl)c4Cl)CC3)cc2N1CO]

by reacting a compound of formula (III)

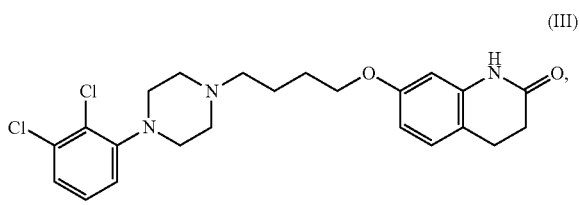 [SMILES: O=C1CCc2ccc(OCCCCN3CCN(c4cccc(Cl)c4Cl)CC3)cc2N1]

which is aripiprazole, or a hydrate thereof, with paraformaldehyde in the presence of a suitable organic solvent and a suitable base, wherein the reaction is carried out either in the absence of water or in the presence of a content of water which comes from either the use of a non-anhydrous organic solvent, non-anhydrous reactants, or the use of a hydrated form of aripiprazole, without addition of further water; and
  b) subsequently converting the compound of formula (II) into aripiprazole lauroxil.

Thus, surprisingly, inventors have found that the process of the invention allows obtaining aripiprazole lauroxil with overall yields unexpectedly higher than the ones obtained by the processes known in the prior art, and at the same time with a high purity, as can be seen from the examples and comparative example. The process is easy to scale-up to an industrial level, and is more cost-effective than the already known processes.

Inventors have also observed that a particular impurity is formed during the process as a result of the reaction of the intermediate compound of formula (II) with formic acid, which is formed as a byproduct in the reaction media.

Thus, according to another aspect of the invention, the isolated compound of formula (IV)

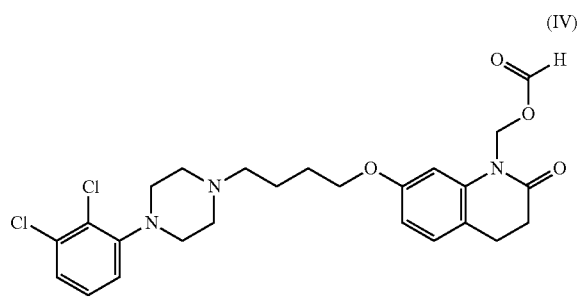 [SMILES: O=COCN1C(=O)CCc2ccc(OCCCCN3CCN(c4cccc(Cl)c4Cl)CC3)cc21]

is provided as a reference standard. The use of the compound of formula (IV) as a reference standard is also part of the invention.

The provision of a method for determining the content of the compound of formula (IV) in an aripiprazole lauroxil sample by high-performance liquid chromatography (HPLC), wherein the compound of formula (IV) is used as a reference compound also forms part of the invention.

DETAILED DESCRIPTION OF THE INVENTION

As used herein, the term "reference standard" refers to a compound that may be used both for quantitative and qualitative analysis of an active pharmaceutical ingredient. For example, the retention time of the compound in HPLC allows for setting a relative retention time, thus making qualitative analysis possible. The concentration of the compound in solution before injection into an HPLC column allows for comparison of the areas under the peaks in an HPLC chromatogram, thus making quantitative analysis possible. For the purposes of the invention, room temperature is 20-25° C.

As mentioned above, aripiprazole lauroxil can be prepared by a process which comprises the steps of: a) preparation a compound of formula (II) as defined above by reacting aripiprazole or a hydrate thereof with paraformaldehyde without the addition of water as a solvent other than the water present in a non-anhydrous solvent, non-anhydrous reactants or a hydrated form of aripiprazole; and b) subsequently converting the compound of formula (II) into aripiprazole lauroxil.

Thus, in step a) water may be added to the reaction mixture indirectly, e.g. as water comprised in the added base or in the solvent, or as water present in a hydrated form of aripiprazole such as aripiprazole monohydrate. In such a case, the amount of water in the reaction mixture should be equal to or lower than 1 wt %.

Conversion of compound of formula (II) into aripiprazole lauroxil can be carried out by using standard esterification methods. Ester formation from alcohols is a chemical reaction well known for a chemist. For instance, esterification can be carried out by reacting alcohols with carboxylic acid, acyl chloride, or acid anhydrides under conventional standard conditions.

Thus, in a particular embodiment of the process of the present disclosure the preparation of aripiprazole lauroxil can be carried out by reacting the compound of formula (II) with lauric acid, lauroyl chloride, or lauric anhydride. The reactions are carried under conventional standard conditions (cf. March, J. Advanced Organic Chemistry, 6th ed., Wiley-VCH, NY, 2007, pp. 1411-1421; Larock, R. C. Comprehensive Organic Transformations, 1st ed., Wiley-VCH, NY, 1989, pp. 966-972).

As an instance, the reaction can be carried out by the classic Fischer esterification, which involves treating a carboxylic acid with an alcohol in the presence of a dehydrating agent. The reaction is usually performed in the presence of a catalyst, such as sulfuric acid. Additionally, a dehydrating agent can be used such as such as molecular sieves. Another example for the dehydration of mixtures of alcohols and carboxylic acids is the Mitsunobu reaction:

$$RCO_2H + R'OH + P(C_6H_5)_3 + R_2N_2 \rightarrow RCO_2R' + OP(C_6H_5)_3 + R_2N_2H_2$$

When performing the reaction between alcohols with acyl chlorides or with acid anhydrides, anhydrous conditions are preferred, since acyl chlorides and acid anhydrides also react with water. Thus, in these reactions, Lewis acids and bases, such as pyridine, 4-(N,N-dimethylamino)pyridine and triethylamine are often used as catalyst.

In a more particular embodiment of the process of the present disclosure, aripiprazole lauroxil can be prepared by reacting a compound of formula (II) as defined above with lauric acid, a carboxyl activating agent in the presence of a suitable solvent and, optionally in the presence of an appropriate base.

Scheme I below illustrates a particular embodiment of the general process of the invention:

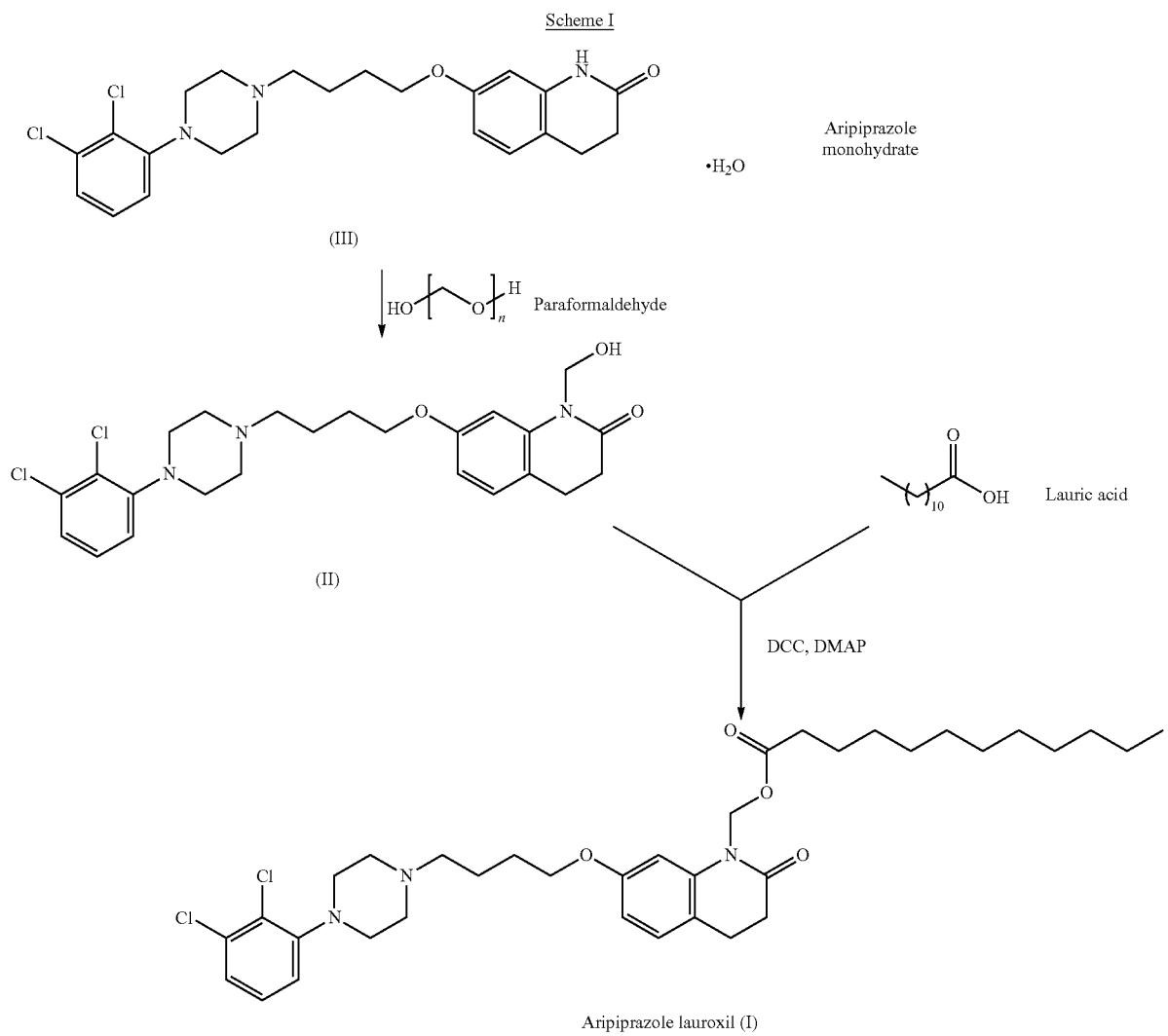

Aripiprazole used as the starting material as such or in form of a monohydrate, paraformaldehyde, and lauric acid are commercially available. Paraformaldehyde (CAS Number 30525-89-4), also known as polyoxymethylene, is a polymer of formaldehyde and can be represented by the chemical formula $(CH_2O)_n$, wherein n is an integer from 8 to 100.

The molar ratio of compound of formula (II) to lauric acid can be from 1:1 to 1:3. More particularly the molar ratio is 1:1.3.

Examples of suitable solvents to carry out the reaction of compound of formula (II) with lauric acid include, without being limited to, toluene, dimethylsulfoxide (DMSO), dimethylformamide (DMF), dimethylacetamide (DMA), tetrahydrofuran (THF), acetone, methyl ethyl ketone (MEK), methyl isobutyl ketone (MIK), dichloromethane (DCM), acetonitrile (ACN), and mixtures thereof. Particularly, the reaction is carried out in dichloromethane.

Examples of carboxyl activating agents include, without being limited to, dicyclohexylcarbodiimide (DCC), diisopropylcarbodiimide (DIC), N-(3-dimethylamino-propyl)-N'-ethylcarbodiimide (EDC), and a combination of one of the previous with a compound selected from the group consisting of N-hydroxysuccinimide or N-hydroxyphthalimide; 1,1'-carbonyldiimidazole (CDI), 1,1'-carbonyl-di-(1,2,4-triazol) (CDT), benzotriazol-1-yloxy-tris(dimethylamino)-phosphonium hexafluorophosphate (BOP), bromo-tripyrrolidino-phosphonium hexafluoro-phosphate (PyBrOP), benzotriazol-1-yloxy-tripyrrolidino-phosphonium hexafluoro-phosphate (PyBOP), 2-(1H-benzotriazol-1-yl)-N,N,N',N'-tetramethylaminium tetrafluoroborate (TBTU), 2-(1H-benzotriazol-1-yl)-N,N,N',N'-tetramethylaminium hexafluorophosphate (HBTU), 2-(7-aza-1H-benzotriazol-1-yl)-N,N,N',N'-tetramethyl-aminium hexafluorophosphate (HATU), and 2-(7-aza-1H-benzotriazol-1-yl)-N,N,N',N'-tetramethylaminium tetrafluoroborate (TATU). Particularly, the reaction is carried out in the presence of dicyclohexylcarbodiimide (DCC), diisopropylcarbodiimide (DIC), N-(3-dimethylamino-propyl)-N'-ethylcarbodiimide (EDC). More particularly the reaction is carried out in the presence of dicyclohexylcarbodiimide (DCC).

Examples of appropriate bases to carry out the reaction of compound of formula (II) with lauric acid include, without being limited to, triethylamine, diisopropylethylamine (DIPEA), N-methylmorpholine (NMM), and dimethylaminopiridine (DMAP). Particularly, the reaction is carried out with 4-dimethylaminopyridine (DMAP).

In a particular embodiment, optionally in combination with one or more features of the particular embodiments defined above or below, the carboxyl activating is dicyclohexylcarbodiimide (DCC) and the base is dimethylaminopiridine (DMAP).

The reaction of compound of formula (II) with lauric acid can be carried out at a temperature from 0° C. to the temperature of the boiling point of the solvent, more particularly, at room temperature.

As mentioned above, compound of formula (II)

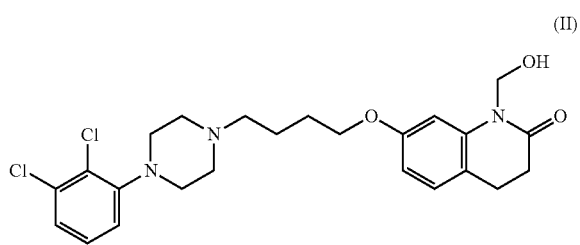

can be obtained by reacting a compound of formula (III)

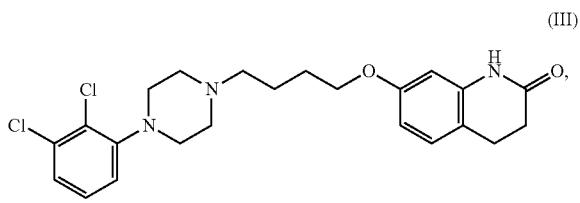

which is aripiprazole, or a hydrate thereof, with paraformaldehyde in the presence of a suitable organic solvent and a suitable base without the addition of water as a solvent to the reaction mixture.

Examples of suitable organic solvents include, without being limited to, toluene, ethyl acetate, dimethylsulfoxide (DMSO), dimethylformamide (DMF), dimethylacetamide (DMA), tetrahydrofuran (THF), acetone, methyl ethyl ketone (MEK), methyl isobutyl ketone (MIK), dichloromethane (DCM), acetonitrile (ACN), and mixtures thereof. Particularly, the organic solvent is toluene.

Examples of bases include, without being limited to, 1,8-diazabicyclo[5.4.0]undec-7-ene, 1,4-diazabicyclo[2.2.2]octane, potassium carbonate, sodium carbonate, cesium carbonate, potassium terbutoxide, and diisopropylethylamine. Particularly, the base is DBU.

In a particular embodiment, as mentioned above, the amount of water present in the reaction mixture comprising aripiprazole and paraformaldehyde is equal to or lower than 1 wt %.

The reaction can be carried out with a molar ratio of aripiprazole, or a hydrate thereof such as the monohydrate, to paraformaldehyde of from 1:1 to 1:3. More particularly the molar ratio is 1:1:1.7.

The intermediate compound of formula (II) mentioned herein above can be used for the following step without further purification or can be effectively separated and purified by employing conventional methods well known to those skilled in the art, such as formation of a slurry, recrystallization, column chromatography, or by transformation into a salt.

In a particular embodiment, the process for the preparation of aripiprazole lauroxil is carried out from aripiprazole or a hydrate thereof without the isolation and/or purification of the intermediate compound of formula (II).

In another particular embodiment, the process for the preparation of aripiprazole lauroxil is carried out from aripiprazole or a hydrate thereof with the purification of the intermediate compound of formula (II).

The presence of the impurity compound of formula (IV) in the final product aripiprazole lauroxil can be reduced to an amount below 0.1% by removing formic acid formed as a side-product during the reaction of aripiprazole or a hydrate thereof and paraformaldehyde and present in the reaction crude comprising the compound of formula (II).

The purification of compound of formula (II) can be carried out by crystallizing or slurring the compound of formula (II) in an appropriate solvent. Particularly, the compound of formula (II) can be purified by slurring in an aqueous media comprising water optionally in the presence of a base such as triethylamine or sodium bicarbonate. Optionally, the impurity, i.e. compound of formula (IV), can be removed by recrystallizing compound of formula (I) by the addition of an alcoholic solvent such as isopropanol, 1-butanol, or ethanol. More particularly the recrystallization is performed in isopropanol.

As mentioned above, compound of formula (IV)

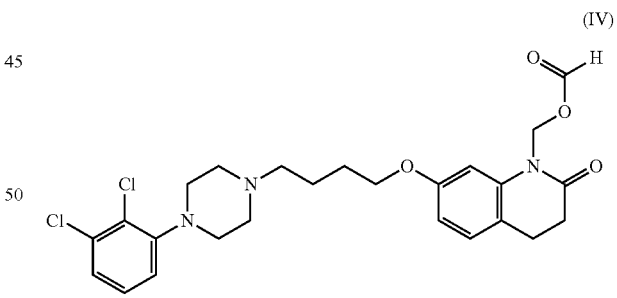

is generated as a side product by reaction of compound of formula (II) with HCOOH, which is formed as a byproduct in the reaction medium.

The isolated compound of formula (IV) is useful as a reference standard for qualitatively or quantitatively determining an impurity in aripiprazole lauroxil, particularly, by high-performance liquid chromatography (HPLC) analysis.

The compound of formula (IV) can be isolated from the crude of aripiprazole lauroxil or, alternatively, it can be prepared from compound (II) by a process comprising:

a) reacting a compound of formula (II)

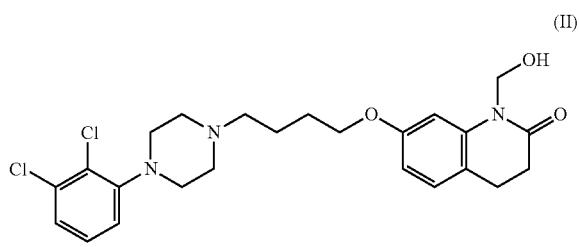 [SMILES: O=C1CCc2ccc(OCCCCN3CCN(c4cccc(Cl)c4Cl)CC3)cc2N1CO]

with formic acid to obtain compound of formula (IV), and
b) isolating the compound of formula (IV) from the reaction medium; and
c) purifying the compound of formula (IV).

Particularly, the compound of formula (IV) can be prepared by a process comprising:
a) reacting a compound of formula (II) as defined above with formic acid and a carboxyl activating agents such as dicyclohexylcarbodiimide in the presence of an appropriate base, such as 4-dimethylaminopyridine, and of a suitable solvent such as dichloromethane;
b) filtering the reaction mixture to obtain a solution containing the compound of formula (IV); and
c) removing the solvent;
c) crystallizing the compound of formula (IV) in isopropanol to obtain a precipitate; and
d) recovering and drying the precipitate to obtain isolated compound of formula (IV).

The present invention also provides a method for determining the content of the compound of formula (IV) in an aripiprazole lauroxil sample by high-performance liquid chromatography analysis (HPLC), wherein the compound of formula (IV) is used as a reference compound, the method comprising the following steps:
preparing a reference solution of the compound of formula (IV) in a pre-determined concentration; preparing a test solution containing aripiprazole lauroxil; obtaining HPLC chromatograms of the reference solution and the test solution by high-performance liquid chromatography analysis respectively; comparing respective retention times in the HPLC chromatograms of the reference solution and the test solution to ascertain that the test solution contains the compound of formula (IV); and determining the content of the compound of formula (IV) in aripiprazole lauroxil in weight percentage by an external standard method.

Additionally, the overall yield from aripiprazole to crude aripiprazole lauroxil range from 80% to 90%.

With the process of the invention aripiprazole lauroxil is obtained with high purity and very good yields. Particularly, aripiprazole lauroxil with a purity of at least 92.9% is obtained.

Aripiprazole lauroxil with a purity of at least 99.5% HPLC can be obtained by submitting the crude product to conventional purification techniques or other techniques described in the prior art such as crystallization, chromatography, or a combination thereof.

In a particular embodiment the compound of formula (I), aripiprazole lauroxil, is purified by crystallization in an alcoholic solvent such as isopropanol, 1-butanol, or ethanol. More particularly the crystallization is performed in isopropanol.

Thus, taking into account all the advantages above mentioned, the alternative process to obtain aripiprazole lauroxil of the present invention can be clearly considered more efficient and advantageous than those previously disclosed in the art.

Throughout the description and claims the word "comprise" and variations of the word, are not intended to exclude other technical features, additives, components, or steps. Furthermore, the word "comprise" encompasses the case of "consisting of". The following examples are provided by way of illustration, and they are not intended to be limiting of the present invention. Furthermore, the present invention covers all possible combinations of particular and preferred embodiments described herein.

EXAMPLES

Example 1

Step 1: Preparation of 7-(4-(4-(2,3-Dichlorophenyl)piperazin-1-yl)butoxy)-1-(hydroxymethyl)-3,4-dihydroquinolin-2(1H)-one (Compound of formula (II)) in toluene and 1,8-diazabicyclo[5.4.0]undec-7-ene (DBU)

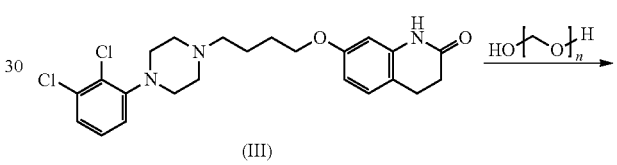

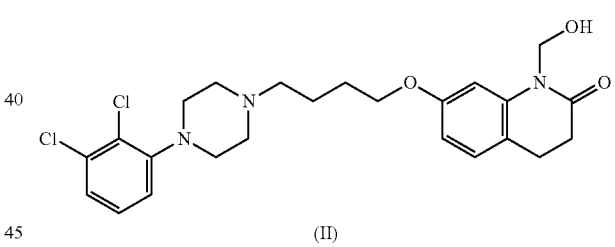

500 mL of toluene (5V), 100.0 g of aripiprazole (as monohydrate) (214 mmol), 10.6 g paraformaldehyde (343 mmol) and 0.65 g DBU (4.29 mmol) were charged into a 1 L reactor, heated to 30-40° C. and kept under stirring and nitrogen atmosphere for 16 hours (until aripiprazole in the reaction mixture is 16.0% HPLC).

The reaction mixture was cooled to T≤5.0° C. and kept for 2 hours at these conditions. The solid was filtered from the mixture, washed once with 100 mL cool toluene. The solid was dried at 30° C. in a vacuum oven for 6 hours to obtain 96.9 g of the title compound (94% yield based on aripiprazole (as monohydrate)). Its purity, analyzed by HPLC was 87.6%, which means a conversion of 82.3%.

The HPLC analysis was carried out in the following column and conditions:
Chromatographic column: XBridge RP Shield C18 (150×3 mm, 3.5 μm);
Column temperature: 40° C.;

Mobile phase: A: 2.3 g $K_2HPO_4 \times 3H_2O$/1 L $H_2O$ pH=6.6$H_3PO_4$ 10%,
B: Acetonitrile
Gradient elution conditions:
The chromatograph was programmed as follows:

| Time (minutes) | Solution A (%) | Solution B (%) | Elution |
|---|---|---|---|
| 0 | 75 | 25 | Isocratic |
| 1.87 | 75 | 25 | Isocratic |
| 18.87 | 15 | 85 | Gradient |
| 22 | 15 | 85 | Isocratic |
| 22.5 | 75 | 25 | Return to initial |
|  | Post-time: 5 min |  | Re-equilibrate |

Main peak retention time: around 15.6 min; Sample volume 2 µL; Detection wavelength: 254 nm; running time: 22 min; Test solution: 1 mg/mL, Solvent: Acetonitrile: Milli-Q water at 10% AcOH (1:2); Column flow: 0.51 ml/min.

Step 2: Purification of Compound of Formula (II)

896 mL of deionized water (10V), 89.6 g of crude (7-(4-(4-(2,3-dichlorophenyl)piperazin-1-yl)butoxy)-1-(hydroxymethyl)-3,4-dihydroquinolin-2(1H)-one are charged into a 2 L reactor, heated to 18-28° C. and kept under stirring and nitrogen atmosphere during at least 30 minutes.

The solid is filtered from the reaction mixture, washed twice with 270 mL deionized water. The solid is dried at 30° C. in a vacuum oven for 16 hours. It is obtained 88.38 g of pure 7-(4-(4-(2,3-dichlorophenyl)piperazin-1-yl)butoxy)-1-(hydroxymethyl)-3,4-dihydroquinolin-2(1H)-one (98.6% yield from crude).

Step 3: Preparation of Aripiprazole Lauroxil (Compound of Formula (I)

Dichloromethane 950 mL, 51.5 g of lauric acid (257 mmol) and 53.0 of N,N-dicyclohexylcarbodiimide (257 mmol) were charged into a reactor and kept under stirring during 10 minutes. Then, 94.6 g of compound of formula (II) obtained in step 1 (198 mmol) and 4.8 g 4-dimethylaminopyridine (39.5 mmol) were charged. The reaction mixture was kept under stirring at room temperature (15-25° C.) for a minimum of 2 hours (until compound of formula (II) in the reaction mixture was ≤0.5% HPLC).

N,N-dicyclohexylurea was filtered from the reaction mixture. Dichloromethane was distilled at reduced pressure (0.7-0.8 bar) until 475 mL of solvent were left in the reaction mixture. Then, 1330 mL of isopropanol were charged and 950 mL of solvent were distilled at reduced pressure. The reaction mixture was cooled to 0-10° C. and kept at this temperature for 2 hours. The mixture was filtered and the solid was washed twice with isopropanol (95 mL). The solid was dried under vacuum at 30° C. for 4 hours to obtain 122 g of aripiprazole lauroxil (93.4% yield) of 92.9% purity (analysed by HPLC).

Three recrystallizations were performed on aripiprazole lauroxil crude using isopropanol as solvent (1200 mL). Finally, 107.9 g of aripiprazole lauroxil (API quality) having a purity of 99.6% (analysed by HPLC) were obtained (82% overall yield from compound of formula (II)).

The HPLC analysis was carried out in the following column and conditions:

Chromatographic column: Gemini C6-phenyl C18 (150× 4.6 mm, 3.0 µm),
Column temperature: 40° C.;
Mobile phase: A: Acetonitrile B: Ammonium acetate pH=7.5

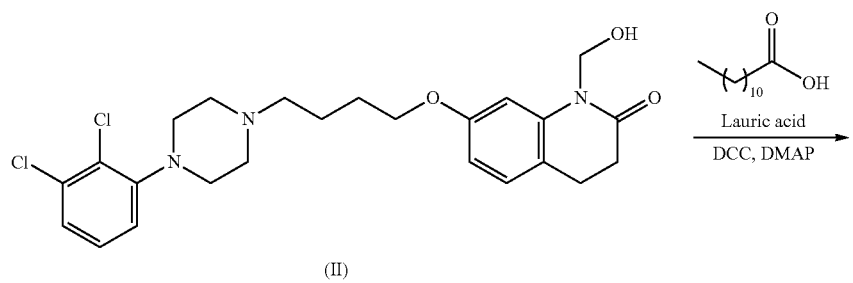

(II)

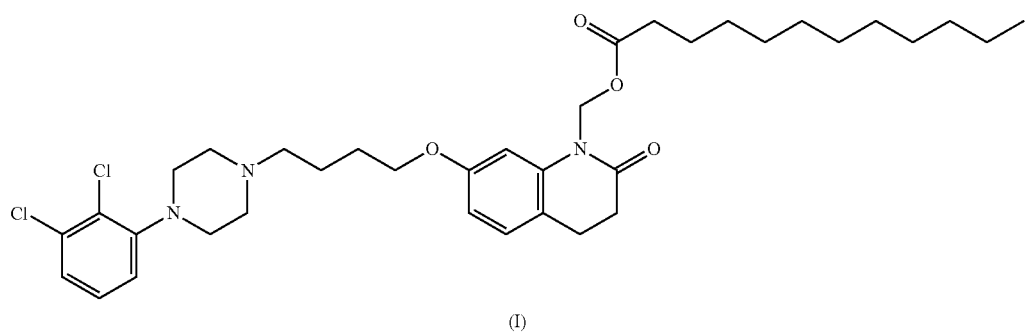

(I)

Gradient elution conditions:
The chromatograph was programmed as follows:

| Time (minutes) | Solution A (%) | Solution B (%) |
|---|---|---|
| 0 | 15 | 85 |
| 5 | 50 | 50 |
| 18 | 75 | 25 |
| 25 | 90 | 10 |
| 35 | 90 | 10 |
| 35.5 | 15 | 85 |
| Post-time: 5 min | | |

Main peak retention time: around 26.7 min; Sample volume 5 µL; Detection wavelength: 215 nm; running time: 35 min; Test solution: 1 mg/mL, Solvent: Acetonitrile: methanol (1:1); Column flow: 1.5 ml/min.

Example 2. Preparation of Compound of Formula (II) in Ethyl Acetate and with Potassium Carbonate 50 mL of ethyl acetate (10V), 5 g of aripiprazole (as monohydrate) (10.72 mmol), 0.48 g of paraformaldehyde (15.97 mmol), and 0.034 g (0.247 mmol) of potassium carbonate were charged into a 100 mL reactor, heated to 38-42° C. and kept under stirring and nitrogen atmosphere during 15 hours (until aripirazole in the reaction mixture was ≤16.0%).
The reaction mixture was cooled to T≤10.0° C. and kept for 1 hour at this condition. The solid was filtered from the mixture, washed once with 5 mL of cool ethyl acetate. The solid was dried at 50° C. in a vacuum oven for 4 hours to obtain 4.69 g of (7-(4-(4-(2,3-dichlorophenyl)piperazin-1-yl)butoxy)-1-(hydroxymethyl)-3,4-dihydroquinolin-2(1H)-one) (91.4% yield based on aripiprazole (as monohydrate)). Its purity, analyzed by HPLC, was 88.0%, which means a conversion of 80.4%.

Example 3. Preparation of Compound of Formula (II) in Acetone and with Potassium Carbonate 10 mL of acetone (10V), 1.03 g of aripiprazole (as monohydrate) (2.14 mmol), 0.099 g of paraformaldehyde (3.29 mmol), and 0.008 g (0.057 mmol) of potassium carbonate were charged into a 50 mL reactor, heated to 20-25° C. and kept under stirring and nitrogen atmosphere during 18 hours (until aripirazole in the reaction mixture was ≤16.0%).
The reaction mixture was cooled to T≤5° C. and kept for 1 hour at this condition. The solid was filtered from the mixture, washed twice with 2.5 mL of cool acetone and twice with 2.5 mL of water. The solid was dried at 50° C. in a vacuum oven for 4 hours to obtain 0.93 g of (7-(4-(4-(2,3-dichlorophenyl)piperazin-1-yl)butoxy)-1-(hydroxymethyl)-3,4-dihydroquinolin-2(1H)-one) (88.0% yield based on aripiprazole (as monohydrate)). Its purity, analyzed by HPLC, was 88.7%, which means a conversion of 77.4%.

Comparative Example 1. Preparation of Compound of Formula (II) in Acetone/Water and with Potassium Carbonate 9 mL of acetone (9V), 1 mL of water (1V), 1.03 g of aripiprazole (as monohydrate) (2.14 mmol), 0.099 g of paraformaldehyde (3.29 mmol), and 0.008 g (0.057 mmol) of potassium carbonate were charged into a 50 mL reactor, heated to 20-25° C. and kept under stirring and nitrogen atmosphere during 18 hours.

A sample of the reaction mixture was taken to perform an HPLC analysis. The result showed that only 2.0% of (7-(4-(4-(2,3-dichlorophenyl)piperazin-1-yl)butoxy)-1-(hydroxymethyl)-3,4-dihydroquinolin-2(1H)-one) was formed and the remaining 98% was aripirazole.

Example 4. Preparation of (7-(4-(4-(2,3-dichlorophenyl)piperazin-1-yl)butoxy)-3,4-dihydro-2-oxoquinolin-1(2H)-yl)methyl formate (Compound of Formula (IV))

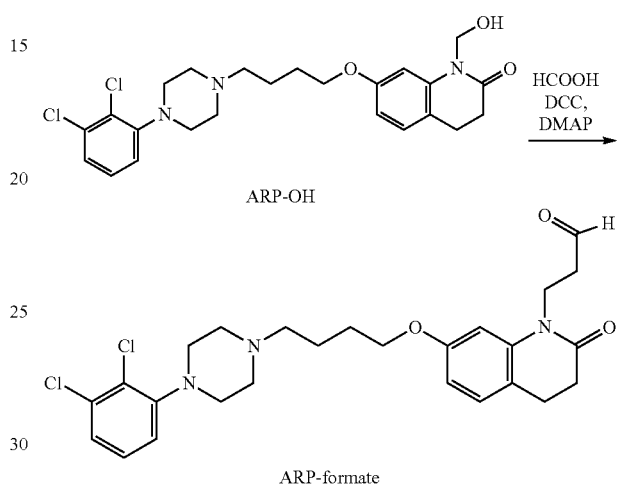

ARP-OH

ARP-formate

Dichloromethane 100 mL, 1.25 g of formic acid (27.2 mmol) and 5.61 g of N,N-dicyclohexylcarbodiimide (27.2 mmol) were charged into a reactor and kept under stirring during 10 minutes. Then, 10 g of compound of formula (II) obtained in Example 1, step 1 (20.90 mmol) and 0.51 g 4-dimethylaminopyridine (4.18 mmol) were charged. The reaction mixture was kept under stirring at room temperature (15-25° C.) for a minimum of 2 hours.
N,N-dicyclohexylurea was filtered from the reaction mixture and washed with 2×20 mL. 90 mL of dichloromethane were distilled at reduced pressure (0.7-0.8 bar). Then, 140 mL of isopropanol were charged and 100 mL of solvent were distilled at reduced pressure. The reaction mixture was cooled to 0-10° C. and kept at 0-10° C. for 2 hour. The mixture was filtered and the solid was washed twice with isopropanol (10 mL). Solid was dried under vacuum at 30° C. for 4 hours to obtain 6.94 g of aripiprazole formate (compound of formula (IV)) (63.8% yield).
Crude aripiprazole formate was suspended in hot isopropanol (65 mL), filtered at 50° C. and dried for 4 hours at 30° C. Aripiprazole formate 94% HPLC pure was obtained (HPLC-MS (M+1)=506).
$^{1}$H-RMN (Bruker; 250 MHz, CDCl$_3$, d (ppm)): 8.17 (s, 1H), 7.17-7.13 (m, 2H), 7.10-7.03 (m, 1H), 6.95 (dd, J=4.2, J=8.0, 1H), 6.63-6.57 (m, 2H), 5.99 (s, 2H), 3.98 (t, J=6.0, 2H), 3.07 (m, 4H), 2.87 (m, 2H), 2.63-2.71 (m, 6H), 2.49 (t, J=7.3, 2H), 1.89-1.75 (m, 2H), 1.74-1.66 (m, 2H).
$^{13}$C-RMN (Bruker; 62.5 MHz, CDCl$_3$, d (ppm)): 170.3, 160.5, 159.0, 151.4, 139.8, 134.1, 128.8, 127.6, 127.5, 124.7, 118.7, 118.3, 108.9, 102.9, 68.1, 67.2, 58.3, 53.4, 51.4, 32.3, 27.4, 24.5. 23.6.
IR (IR-ATR; Nicolet Series IS5 (Thermo, cm$^{-1}$): 2945, 2813, 1714, 1690, 1612, 1349, 1133, 1067.

The same HPLC method as for aripiprazole lauroxil was used. The HPLC-MS analysis was carried out in the following column and conditions:

Mobile Phase
  Solution A: Acetonitrile
  Solution B: Buffer
  Buffer: Prepare a solution containing 0.77 g ammonium acetate in 950 mL of water. Adjust pH to 7.5 with 1% ammonia solution and dilute to 1.0 L with water. Pass through a filter having a 0.22 μm and degas.

| HPLC-MS Chromatographic conditions. | |
| --- | --- |
| Column | Gemini C6 phenyl (150 × 4.6 mm, 3.0 μm) |
| Flow (mL/min) | 1.5 |
| Oven temperature (° C.) | 40 |
| D.A.D. wavelength (nm) | 215 |
| Injection volume | 5 μL |
| MSD Parameters. spectrometer (Agilent, 6130 MS) | Mass detector |
| Ionitzation mode | API-ES |
| Polarity | Positive |
| Mass range | 100-2000 |
| Fragmentor | 70 V |
| Gain EMV | 1.0 |
| Threshold | 150 |
| Gas Temp | 350° C. |
| DryingGas | 12.0 l/min |
| Neb Pres | 60 psig |
| V Cap (+) | 3000 V |

The chromatograph is programmed as follows.

| Time (minutes) | Solution A (%) | Solution B (%) |
| --- | --- | --- |
| 0 | 15 | 85 |
| 5 | 50 | 50 |
| 18 | 75 | 25 |
| 25 | 90 | 10 |
| 35 | 90 | 10 |
| 35.5 | 15 | 85 |
| 39.5 | 15 | 85 |

CITATION LIST

1. EP367141
2. WO2010151689
3. WO2016032950
4. March, J. Advanced Organic Chemistry, 6th ed., Wiley-VCH, NY, 2007, pp. 1411-1421;
5. Larock, R. C. Comprehensive Organic Transformations, 1st ed., Wiley-VCH, NY, 1989, pp. 966-972.

The invention claimed is:

1. An isolated compound of formula (IV)

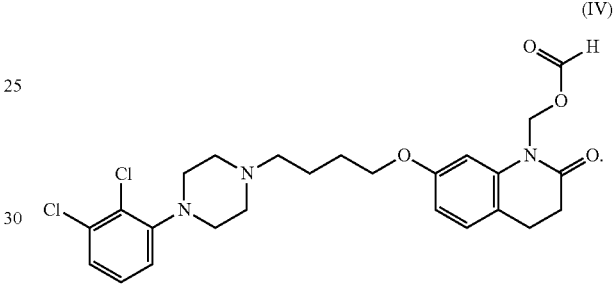

(IV)

2. A method for determining the content of an impurity in aripiprazole lauroxil sample by high-performance liquid chromatography analysis, wherein the compound of formula (IV) as defined in claim 1 is the impurity used as a reference compound.

* * * * *